United States Patent [19]

Zörner

[11] Patent Number: 5,445,027
[45] Date of Patent: Aug. 29, 1995

[54] METHOD AND APPARATUS FOR DETECTING AND LOCATING DEFECTS IN A COMPONENT OF A TURBINE

[75] Inventor: Walter Zörner, Baiersdorf, Germany

[73] Assignee: Siemens Aktiengesellschaft, Munich, Germany

[21] Appl. No.: 198,882

[22] Filed: Feb. 17, 1994

[63] Belated U.S. Application Data Continuation of PCT/DE92/00607, July 24, 1992.

[30] Foreign Application Priority Data

Aug. 19, 1991 [DE] Germany ............ 41 27 395.8

[51] Int. Cl.[6] .................. G01H 13/00; G01M 13/00; G01N 29/12
[52] U.S. Cl. ............................ 73/593; 73/629; 73/660
[58] Field of Search ............. 73/579, 583, 587, 593, 73/627, 629, 589, 660

[56] References Cited

U.S. PATENT DOCUMENTS

| | | | |
|---|---|---|---|
| 3,416,630 | 12/1968 | Pohl et al. | 73/593 |
| 4,007,630 | 2/1977 | Noda | 73/593 |
| 4,685,335 | 8/1987 | Sato et al. | 73/587 |
| 4,977,516 | 12/1990 | Shepherd | 364/508 |
| 5,070,722 | 10/1991 | Hawman et al. | 73/28.01 |
| 5,152,172 | 10/1992 | Leon et al. | 73/579 |

FOREIGN PATENT DOCUMENTS 0209862  1/1987  European Pat. Off. .

OTHER PUBLICATIONS

"Koerperschall–und Schwingungsanalysen . . . ", VGB Kraftwerkstechnik, Issue 9, Sep. 1989, pp. 896–907.

*Primary Examiner*—Hezron E. Williams
*Assistant Examiner*—Rose M. Finley
*Attorney, Agent, or Firm*—Herbert L. Lerner; Laurence A. Greenberg

[57] ABSTRACT

In a method for the early detection and location of a change in a component of a turbine, in particular in a turbine blade, in the event of a deviation from a standard value in at least one measured value determined during operation of the turbine, an acoustic spectrum generated by the component is measured in the interior of the turbine and compared with a reference spectrum. In order to increase the intensity of signals in the acoustic spectrum, the components of the turbine, preferably runner blades, are excited from outside to acoustic emission (resonance test). An apparatus has a number of sensors for recording operating parameters of the turbine. The sensors are connected to a device for measured value conditioning. In order to detect and locate changes, an acoustic measurement probe which can be inserted from the outside into the interior of the turbine, is connected to the device.

17 Claims, 3 Drawing Sheets

METHOD AND APPARATUS FOR DETECTING AND LOCATING DEFECTS IN A COMPONENT OF A TURBINE

CROSS-REFERENCE TO RELATED APPLICATIONS

This application is a continuation of International Application Serial No. PCT/DE92/00607, filed July 24, 1992.

BACKGROUND OF THE INVENTION

Field of the Invention

The invention relates to a method for the detection and location of changes in a component of a turbine, in particular in a turbine blade. It is directed, furthermore, to an apparatus for carrying out the method.

During operation of a turbine, for example a steam turbine, a measurable sound spectrum or acoustic spectrum (structure-borne noise) is emitted as a consequence of a reaction of individual components, in particular of the turbine blade, to different stresses. Such stresses are, for example, forces and temperature differences occurring during the expansion of a working agent. In addition, due to the energy conversion in the turbine, pressure fluctuations are produced which likewise lead to a characteristic acoustic emission of the components and are expressed in the so-called blade rotating noise. Irregularities in the operation of the turbine such as, for example, grazing of the runner blades of the turbine against the housing or against adjacent guide blades, or a loose turbine blade, also cause a disturbance-specific acoustic emission having a wide acoustic spectrum. The signal components in that acoustic spectrum differ with respect to the frequency and the intensity of the emitted acoustic energy and are characteristic for a turbine in normal operation, that is to say in fault-free operation, with the acoustic spectrum ranging from infrasound to ultrasound.

A method for determining and analyzing such acoustic emissions is disclosed in the publication entitled VGB Kraftwerkstechnik, Issue 9, September 1989, pages 899 to 907. Examples of a typical acoustic spectrum measured on the turbine housing and of an associated reference spectrum are represented in a simplified fashion in FIGS. 4 and 5, respectively. In the normal state of the turbine, characteristic signals, for example specific harmonic oscillations or frequencies f of the runner blade rotating noise having different intensities I emerge clearly, in the case of so-called structure-borne noise, from the reference spectrum represented in FIG. 5. In the case of the acoustic spectrum represented in FIG. 4, further signals are present in addition at different frequencies f having different intensities I. Those further signals are characteristic of specific changes, for example of the lack of turbine blades, or of a gear error in a gear disposed between the turbine and a generator.

In the known method, apart from the measurement of the structure-borne noise or blade rotating noise on the turbine housing, during operation of the turbine further measured values, for example the pressure and the temperature in the interior of the turbine, are determined and compared with standard values or desired values determined during fault-free operation of the turbine. In the event of a desired value deviation, a characterization of a coarse change which is present is possible by comparison with empirically determined faults or disturbances. However, early detection and exact location of a change which is only slowly proceeding in a specific component of the turbine are not possible, using that method. Consequently, to date damage has frequently not been detected until consequential damage had occurred and it had therefore been necessary to shut down the turbine at once. However, such an unscheduled shut down of a turbine, followed by an expensive fault-finding operation with the turbine housing open leads to down times which are extremely undesirable.

SUMMARY OF THE INVENTION

It is accordingly an object of the invention to provide a method and an apparatus for the detection and location of changes in a component of a turbine, which overcome the hereinafore-mentioned disadvantages of the heretofore-known methods and devices of this general type, in which the method makes reliable and early fault detection possible and in which this is achieved with regard to a technical outlay that is as small as possible by means of a particularly suitable device.

With the foregoing and other objects in view there is provided, in accordance with the invention, a method for the detection and location of changes in a component of a turbine, in particular a turbine blade, which comprises determining at least one measured value during operation of a turbine; and determining an acoustic spectrum generated by a component of the turbine with a probe in the interior of the turbine and comparing the acoustic spectrum with a reference spectrum, in the event of a deviation from a standard value in the at least one measured value determined during operation of the turbine.

A measured value deviation from a corresponding standard value, for example in the pressure, the temperature or the acoustic spectrum occurring during operation, initially permits a course change to be determined or detected on one hand, and permits the number of possible faulty components to be limited on the other hand. Determination of the acoustic spectrum in the interior of the turbine, that is to say measuring the acoustic emission directly at the component, furthermore permits detailed fault detection.

In accordance with another mode of the invention, in order to increase the signal intensities of the acoustic spectrum determined in the interior of the turbine, the components are excited from outside to acoustic emission, for example in the form of a so-called resonance test of the turbine blades with the aid of a sound or acoustic generator. An exact location of the relevant component is achieved by the subsequent comparison of the acoustic spectrum measured directly in the interior of the turbine or generated by the excitation with a reference spectrum from the initial state of the turbine. In addition, the degree of the change or of the damage, in particular including an expansion of a crack already present, is detected early, so that it is possible to remove the damage, for example during times of low energy requirement, in the time before complete failure of the relevant component.

In accordance with a further mode of the invention, the surface of the component is illuminated stroboscopically and the image produced in the process is recorded, with the stroboscopic illumination expediently being synchronized with a suitable speed of the turbine. The image recorded in the process is compared with a reference image of the same component. This measure is particularly suitable for the case in which a change is produced in a visually accessible region of the component because of a preceding excitation of the component.

In accordance with an added mode of the invention, a movable ultrasonic generator is brought up to a visually inaccessible region of the component and is lead there along at least one part of the circumference of the component. This is done if a change is present in the visually inaccessible region of the component, for example a crack on a turbine blade or on an impeller, for example because of a preceding excitation of the component.

In accordance with an additional mode of the invention, there is provided a method which comprises recording a reference spectrum on a turbine housing, recording an acoustic spectrum occurring during operation on the turbine housing as a measured value, comparing the acoustic spectrum with the reference spectrum, and storing the acoustic spectrum.

With the objects of the invention in view, there is also provided an apparatus for the detection and location of changes in a component of a turbine, in particular in a turbine blade, comprising a device for measured value conditioning of a turbine; a plurality of sensors being connected to the device for recording operating parameters of the turbine; and an acoustic measurement probe being connected to the device and being insertable from the outside into the interior of the turbine.

In accordance with another feature of the invention, the probe is connected to an adjusting device for vertically displacing and rotating the probe.

In accordance with a concomitant feature of the invention, in order to excite sound from the turbine blades, there is provided a flexible head on the free end of the probe being brought into contact with the runner blades.

Other features which are considered as characteristic for the invention are set forth in the appended claims.

Although the invention is illustrated and described herein as embodied in a method and an apparatus for the detection and location of changes in a component of a turbine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
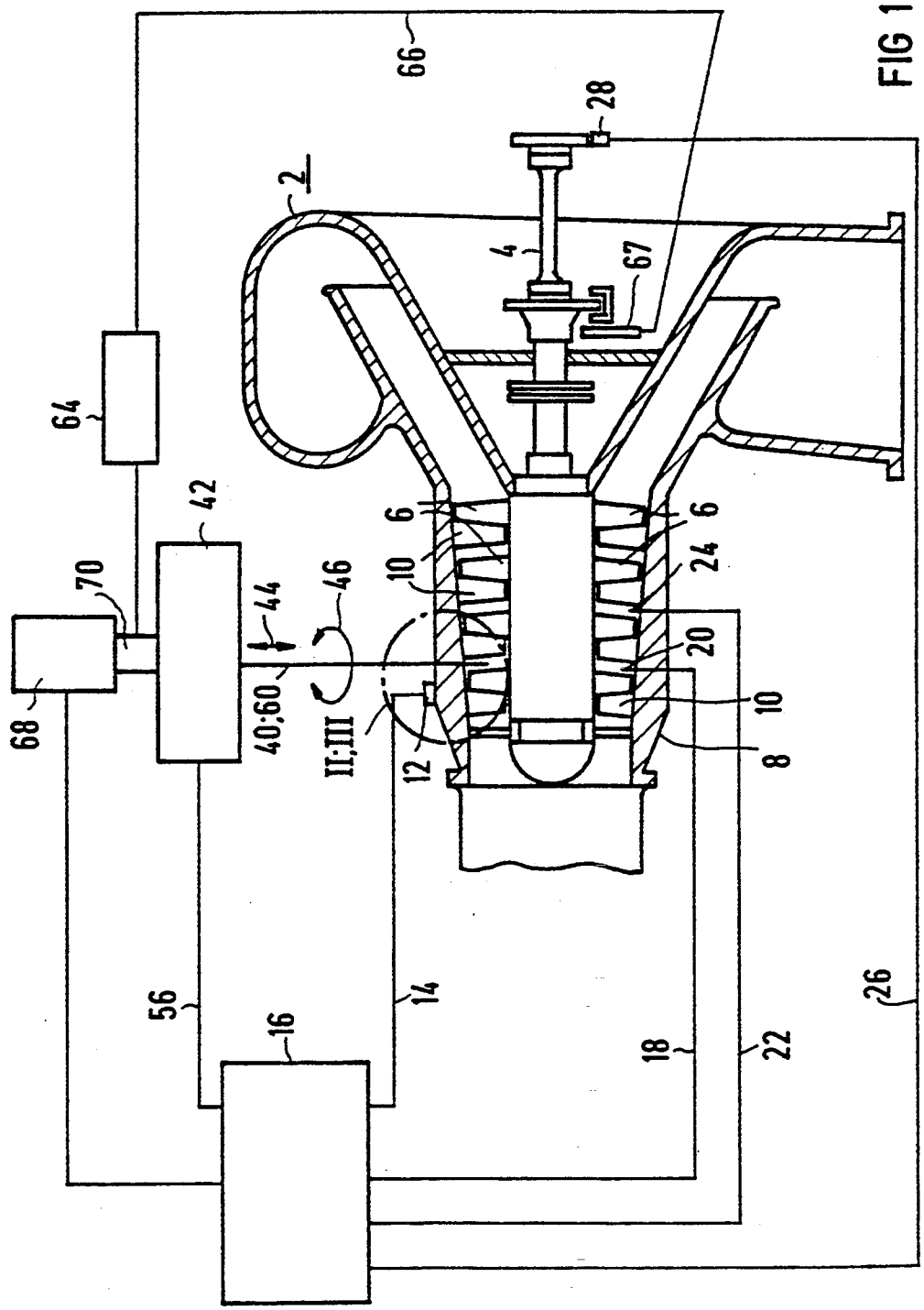
FIG. 1 is a fragmentary, diagrammatic, sectional view with a schematic circuit diagram of a device for carrying out a method according to the invention.

Referring now in detail to the figures of the drawing, in which mutually corresponding parts are provided with the same reference numerals, and first, particularly, to FIG. 1 thereof, there is seen a turbine 2 which includes rotating blades 6 mounted on a shaft 4, and guide blades 10 connected to a turbine housing 8.

Mounted on the turbine housing 8 is a sensor 12 for recording acoustic emission from the turbine 2 during operation. The acoustic emission is so-called structure-borne noise or blade rotating noise. The sensor 12 is connected by a line 14 to a device 16 for measured value conditioning.

Moreover, the device 16 for measured value conditioning receives a measured value determined by a temperature sensor 20 over a line 18, it receives a measured value determined by a pressure sensor 24 over a line 22, and it receives a measured value determined by a strain sensor 28 over a line 26. The strain sensor 28 measures an axial strain of the shaft 4, which indicates a grazing process, that is to say contact of a runner blade 6 with a guide blade 10 or with the housing 8, if a change is simultaneously determined by the sensor 12 in the blade rotating noise. A high measurement accuracy is achieved by such a coherence of two standard value deviations.

Figure 2:
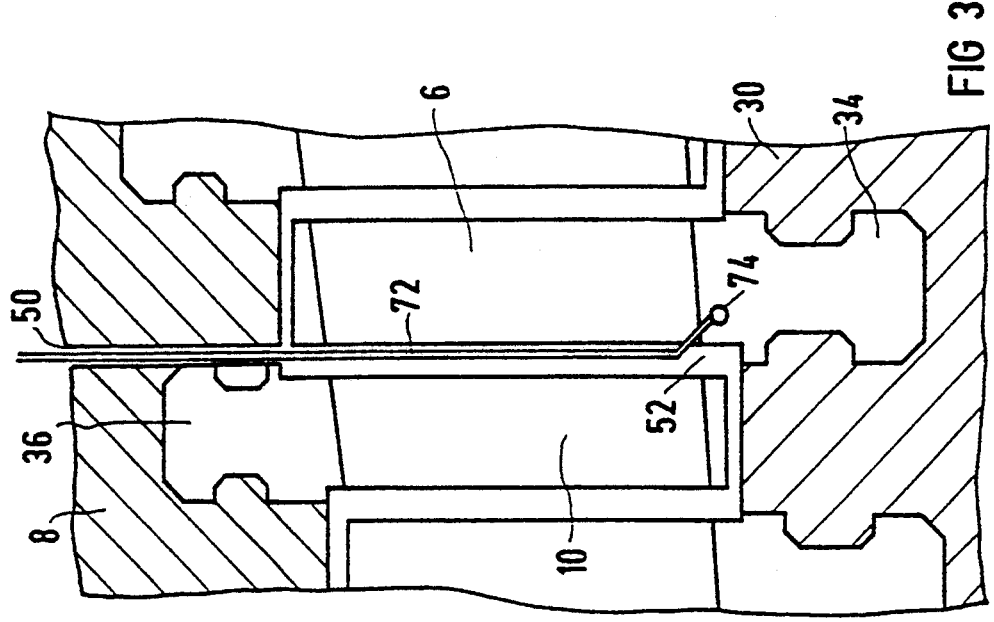
FIG. 2 is an enlarged, sectional view of a portion II of FIG. 1 with a probe inserted into a turbine.
Figure 3:
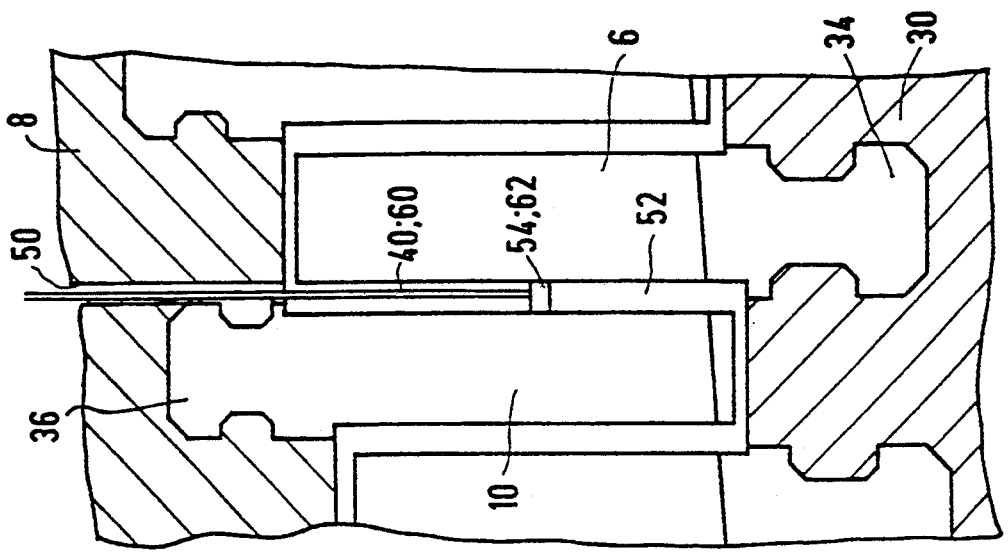
FIG. 3 is a sectional view of a portion III of FIG. 1 having an ultrasonic generator inserted into the turbine.
Figure 4:
FIGS. 4 and 5 are simplified graphical representations of sound spectra measured on a turbine housing or in an interior of the turbine.
Figure 5:
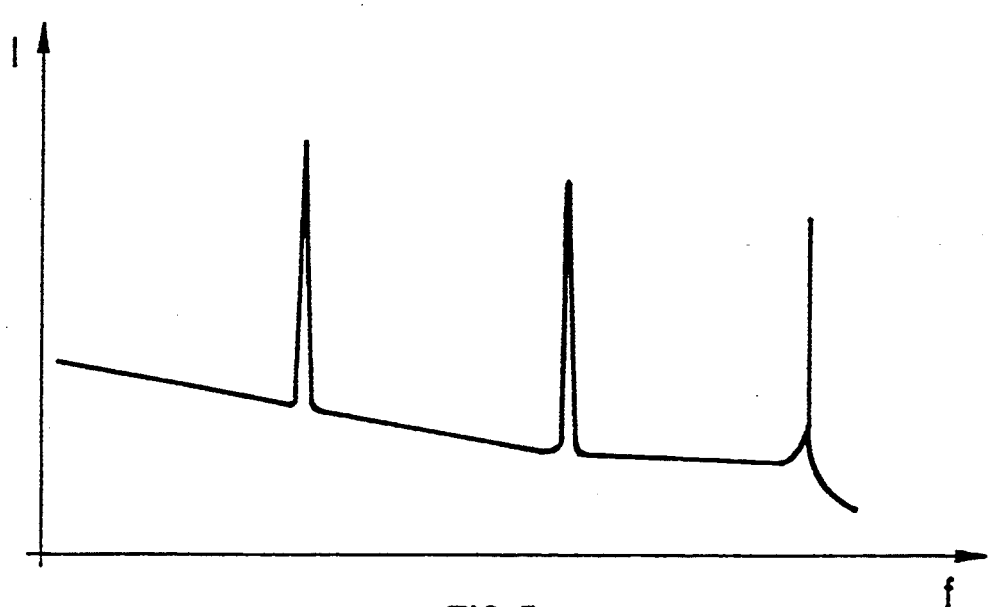

If a change is detected in a component of the turbine 2, in particular in a row of runner blades, in a row of guide blades or in an impeller 30 seen in FIGS. 2 and 3, because of a deviation in one of the measured values determined by the sensors 20, 24, 28, it is initially possible to make a statement on the type of a disturbance and to limit the number of possibly affected components 6, 10, 30. Thus, for example, it is possible with the aid of a comparison of an acoustic spectrum, recorded by the sensor 12 in accordance with FIG. 5, with a reference spectrum stored in the device 16 for measured value conditioning in accordance with FIG. 4, to determine a crack in a runner blade 6 or a guide blade 10. Such a crack is reflected in a pressure or temperature variation as well. If, by contrast, only a slight change is detected, which only permits suspicion of a specific component, such as, for example, suspicion of a crack on a runner blade 6 or a guide blade 10, or on a blade root 34 or 36 seen in FIGS. 2 and 3, respectively, then an acoustic recording is initially carried out in the interior of the turbine 2 and, if necessary, a resonance test is carried out by exciting the runner blade 6 to acoustic emission from outside. This is described in more detail below. Such a crack or incipient crack, which frequently expands slowly, can be produced, for example, by stress crack corrosion or during a grazing process. In this case, what is initially detected in the acoustic spectrum recorded by the sensor 12 is only the grazing process itself, but not slight damage attended by substantial consequential damage possibly occurring at a later time.

For the purpose of detecting such very small changes in a blade 6 or 10, in a blade root 34 or 36, or in an impeller 30 on which the runner blades 6 are mounted in a row of blades, at specific speeds a probe 40 for acoustic recording is inserted from the outside through the housing 8 into the turbine 2, during operation of the turbine 2. For this purpose, the probe 40 is connected to an adjusting device 42 by means of which it is possible to carry out a vertical displacement or a rotary movement of the probe 40, as is indicated by arrows 44 and 46. In FIG. 2 the probe 40 which is represented is guided through an opening 50 in the housing 8 into a gap 52 that is present between the runner blades 6 and the guide blades 10 of a stage of the turbine 2. In a non-illustrated, corresponding way, the probe 40 can also be guided on the blades 6, 10 of adjacent turbine stages, with appropriate housing openings likewise being provided there.

Mounted on a free end of the probe 40 is a flexible head 54 which is brought into contact with the rotating runner blades 6 of the turbine 2 for the purpose of excitation. This process is denoted as a resonance test. The acoustic spectrum emitted in this case is recorded by the probe 40, which is suitable for acoustic recording, and is transmitted over a line 56 to the device 16. Given adequate intensity, signal components of the acoustic spectrum generated by the excitation are also present in the acoustic spectrum occurring during operation and being measured by the sensor 12 on the housing 8.

The acoustic spectrum being generated by the components 6, 10 directly or due to the resonance test, is compared in the device 16, for example with the aid of a computer, with a stored reference spectrum from the initial state of the turbine 2. In this case, a signal being contained in the acoustic spectrum and lacking in the reference spectrum corresponds to a characteristic which is, for example, an empirically determined, change in a component, for example in a runner blade 6. It is possible on the basis of a periodically recurring signal to determine from the recorded acoustic spectrum which runner blade 6 has a change, with it being the case that a signal characteristic of each runner blade 6 likewise occurs periodically and that each blade 6 can thus be identified with the aid of the acoustic spectrum. By applying the head 54 or a similar sound generator to a runner blade 6, it is possible in a similar way to determine a change in a guide blade 10, with it being the case that the head 54 corotating with the runner blades 6 is in contact with the guide blades 10 and acts to excite acoustic emission.

In the case of such a resonance test, that is to say due to an excitation of the turbine blades 6 or 10 to acoustic emission, a change may be determined in a visually accessible region of the component, for example in a specific runner blade 10. In such a case, instead of the probe 40 for acoustic recording, a probe head 62 disposed on a glass fiber cable 60 for the transmission of light is inserted into the gap 52 and guided, in a selected speed range of the turbine 2, along the turbine blade 6 by means of the adjusting device 42. In this process, the surface of the turbine blade 6 is illuminated by means of light pulses generated by a light source or stroboscope 64 and is guided through the glass fiber cable 60. The frequency of the light pulses are synchronized with the speed of the turbine 2. For this purpose, the stroboscope 64 is connected by a line 66 to a tachometer 67. Any desired runner blade 6 can be selected and illuminated through the synchronization. The images of the surface of the runner blade 6 produced in this case are transmitted through the probe head 62 and the glass fiber cable 60 to a camera 68 having a focus 70. The images recorded by the camera 68 are transmitted for the purpose of comparison with stored reference images to the device 16 for measured value conditioning.

If it is found on the basis of an excitation of the runner blades 6 that a change is present in a visually inaccessible region, in particular in a blade root 34, instead of the glass fiber cable 60 with the probe head 62, as is represented in FIG. 3, an ultrasonic generator 74 mounted on a flexible cable 72 is brought up through the gap 52 to the blade root 34 when the turbine 2 is shut down. The ultrasonic generator 74 is guided there along the periphery of the blade root 34 in order to detect a crack.

The acoustic spectra recorded in the interior of the turbine 2 have different signals, depending on the type and extent of the change. However, the spectra are very similar to the acoustic spectra represented in simplified form in FIGS. 4 and 5, and are therefore not represented separately.

I claim:

1. A method for detecting and locating defects in a component of a turbine, which comprises:
   determining at least one measured value during operation of a turbine;
   comparing the at least one measured value to a standard for detecting a defect; and
   when a deviation from the standard value in the at least one measured value is determined during operation of the turbine, inserting a probe into the interior of the turbine; and
   measuring a first acoustic spectrum generated by a component of the turbine with the probe and comparing the first acoustic spectrum with a first reference spectrum to locate the defect.

2. The method according to claim 1, which comprises generating a second acoustic spectrum at the component by excitation from outside of the turbine, before the measurement of the second acoustic spectrum, if a deviation from the standard value in the at least one measured value is determined during operation of the turbine, and comparing the second acoustic spectrum with a second reference spectrum.

3. The method according to claim 1, which comprises stroboscopically illuminating a surface of the component generating the first acoustic spectrum, after the measurement of the first acoustic spectrum, recording an image being generated, and comparing the recorded image with a reference image.

4. The method according to claim 2, which comprises stroboscopically illuminating a surface of the component generating the second acoustic spectrum, after the measurement of the second acoustic spectrum recording an image being generated, and comparing the recorded image with a reference image.

5. The method according to claim 1, which comprises bringing a movable ultrasonic generator up to a visually inaccessible region of the component, after the measurement of the first acoustic spectrum, and if the turbine is shut down, and leading the ultrasonic generator along at least one part of a periphery of the component.

6. The method according to claim 2, which comprises bringing a movable ultrasonic generator up to a visually inaccessible region of the component, after the measurement of the second acoustic spectrum, and if the turbine is shut down, and leading the ultrasonic generator along at least one part of a periphery of the component.

7. The method according to claim 1, which comprises recording a third reference spectrum on a turbine housing, and storing the third reference spectrum as a standard value, recording a third acoustic spectrum occurring during operation on the turbine housing as a measured value, and comparing the third acoustic spectrum with the third reference spectrum.

8. The method according to claim 2, which comprises recording a third reference spectrum on a turbine housing, and storing the third reference spectrum as a standard value, recording a third acoustic spectrum occurring during operation on the turbine housing as a measured value, and comparing the third acoustic spectrum with the third reference spectrum.

9. The method according to claim 3, which comprises recording a third reference spectrum on a turbine housing, and storing the third reference spectrum as a standard value, recording a third acoustic spectrum occurring during operation on the turbine housing as a measured value, comparing the third acoustic spectrum with the third reference spectrum.

10. The method according to claim 5, which comprises recording a third reference spectrum on a turbine housing, and storing the third reference spectrum as a standard value recording a third acoustic spectrum occurring during operation on the turbine housing as a measured value, and comparing the third acoustic spectrum with the third reference spectrum.

11. A method for detecting and locating defects in a turbine blade of a turbine, which comprises:
   determining at least one measured value during operation of a turbine;
   comparing the at least one measured value to a standard value for detecting a defect; and
   when a deviation from the standard value in the at least one measured value is determined during operation of the turbine, inserting a probe into the interior of the turbine; and
   measuring an acoustic spectrum generated by a turbine blade of the turbine with the probe and comparing the acoustic spectrum with a reference spectrum to locate the defect.

12. An apparatus for detecting and locating defects in a component of a turbine, comprising:
   a device for measured value conditioning of a turbine;
   a plurality of sensors being connected to said device for recording operating parameters of the turbine for detecting a defect; and
   an acoustic measurement probe being connected to said device and being insertable from the outside into the interior of the turbine for locating the defect.

13. The apparatus according to claim 12, including an adjusting device for vertically displacing and rotating said probe.

14. The apparatus according to claim 12, wherein said probe has a free end, and including a flexible head on said free end for exciting sound from turbine blades of the turbine.

15. The apparatus according to claim 13, wherein said probe has a free end, and including a flexible head on said free end for exciting sound from turbine blades of the turbine.

16. The apparatus according to claim 12, wherein said device includes means for determining at least one measured value during operation of the turbine, means for determining an acoustic spectrum generated by a component of the turbine with said probe, if a deviation from a standard value in the at least one measured value is determined during operation of the turbine, and means for comparing the acoustic spectrum with a reference spectrum.

17. An apparatus for detecting and locating of defects in a turbine blade of a turbine, comprising:
   a device for measured value conditioning of a turbine;
   a plurality of sensors being connected to said device for recording operating parameters of the turbine for detecting a defect; and
   an acoustic measurement probe being connected to said device and being insertable from the outside into the interior of the turbine for locating the defect.

* * * * *